(12) United States Patent
Green et al.

(10) Patent No.: US 10,758,808 B2
(45) Date of Patent: Sep. 1, 2020

(54) ATHLETICISM RATING AND PERFORMANCE MEASURING SYSTEMS

(71) Applicant: Universal Athletic Testing, LLC, Tampa, FL (US)

(72) Inventors: Obioma Victor Green, Tampa, FL (US); James Philip Dawson, Tampa, FL (US)

(73) Assignee: UNIVERSAL ATHLETIC TESTING, LLC, Tampa, FL (US)

( * ) Notice: Subject to any disclaimer, the term of this patent is extended or adjusted under 35 U.S.C. 154(b) by 66 days.

(21) Appl. No.: 16/030,099

(22) Filed: Jul. 9, 2018

(65) Prior Publication Data

US 2020/0009440 A1    Jan. 9, 2020

(51) Int. Cl.
*G06F 17/00* (2019.01)
*A63B 71/06* (2006.01)

(52) U.S. Cl.
CPC .................. *A63B 71/06* (2013.01)

(58) Field of Classification Search
CPC ............ A63B 24/0006; A63B 24/0062; A63B 2024/0009; A63B 2024/0012; A63B 2024/0065; A63B 2024/0068; A63B 2024/0071; A63B 1/0616; A63B 1/0669; G07F 17/3276
See application file for complete search history.

(56) References Cited

U.S. PATENT DOCUMENTS

| | | |
|---|---|---|
| 7,416,489 B2 | 8/2008 | Smith, III |
| 8,162,804 B2 | 4/2012 | Tagliabue |
| 8,447,420 B2 | 5/2013 | Bloodworth |
| 8,538,910 B2 | 9/2013 | Minka et al. |
| 8,620,585 B2 | 12/2013 | Graham et al. |
| 8,649,890 B2 | 2/2014 | Martin |
| 8,825,445 B2 | 9/2014 | Hoffman et al. |
| 8,944,921 B2 | 2/2015 | Knapp et al. |
| 2006/0205566 A1 | 9/2006 | Watterson |
| 2012/0130515 A1* | 5/2012 | Homsi ................ G06F 19/3481 700/91 |
| 2017/0080279 A1* | 3/2017 | Arredondo ........... A61B 5/6892 |

\* cited by examiner

*Primary Examiner* — Lawrence S Galka
(74) *Attorney, Agent, or Firm* — Stanton IP Law Firm, P.A.

(57) ABSTRACT

An athleticism rating system and related athletic performance measuring systems is described. The athleticism rating system evaluates individual athletes against an athletes' definable skill tests which are common such as weight lifting, running or cycling times or standardized tests or a custom set of athletic performance tests. The related performance measuring system preferably is a user configurable software system that is configurable to be used on a computer system such as a laptop or desktop, smart phone or tablet and it ensures quick, easy, and accurate collection of athletic event data. In one disclosed embodiment, the performance rating system provides seamless athletic data collection and rating of athletes.

8 Claims, 5 Drawing Sheets

ATHLETICISM RATING AND PERFORMANCE MEASURING SYSTEMS

STATEMENT REGARDING FEDERALLY SPONSORED RESEARCH OR DEVELOPMENT

The research for the Patent "Athleticism rating and performance measuring systems" was not funded by any federally sponsored research or development.

DESCRIPTION

Field of Disclosure

This invention relates generally to athleticism rating and related performance measuring systems for use primarily with athletic activities such as training and evaluating athletes and the like.

Background of the Invention

The role of athletics in the modern society is important both from a health role and a training role for our youth. In addition to competing against each other on the field, athletes often compete with each other off the field. For example, student athletes routinely compete with each other for a spot on the team, or even if they are already on the team, for more "game time" or a higher starting position. Graduating high school seniors are also in competition with other student athletes for college athletic scholarships. Additionally, the range of amateur athletes also have various competitions and they often compete with each other for jobs as professional athletes in a given sport, for endorsements from manufacturers of sporting goods and other related products. The critical factor in all of these competitions is the athletic performance, or athleticism, of the particular athlete, and the ability of that athlete to demonstrate or document those abilities to others.

Speed, agility, strength, and endurance are some of the determining characteristics influencing the athleticism of an athlete. Having a method to accurately measure these characteristics is a means of quantifying an individual with respect to their competitors. The comparison process drives athletes to strive to improve their athletic performance in these areas, and coaches and recruiters to rate the individuals on the same basis so that they can select those athletes for their teams which have the best set of these characteristics for their particular sport. In sports, it is common for teams to attempt to select the best athlete when adding team members to provide strength to their overall roster and a tool such as the instant invention which would assist them would be helpful to achieve the best mixture of team members for their team.

Currently the state of comparison of athletic ability and the resulting evaluation and comparison of athletes has been largely subjective. Scouts tour all over the world viewing potential athletes for their team. The main issue is that the methods for evaluating and recruiting athletes are usually hit or miss and it does not provide a means for an athlete to identify issues so that they can address weakness in a performance area.

One method for evaluating and comparing athletes' athleticism involves having the athletes perform a common set of exercises and drills. Athletes that perform the exercises or drills more quickly and/or more accurately are usually considered to be better than those with slower or less accurate performance for the same exercise or drill. For example, "cone drills" are routinely used in training and evaluating athletes. In a typical "cone drill" the athlete must follow a pre-determined course between several marker cones and, in the process, execute a number of rapid direction changes, and/or switch from forward to backward or lateral running.

Although widely used in many institutions, high schools, colleges, training camps, and amateur and professional teams, such training and testing drills usually rely on the subjective evaluation of the coach or trainer.

The system also lacks the ability to stratify athletes based on age and skill levels so that they can adequately be compared over a group of individual athletes with various skill sets and their scores normalized so that performance within a category is identified and that the skill level over the total category is presented to the observer.

Moreover, efforts to meaningfully compile and evaluate the results of the various competitive exercises and drills have been limited. For example, while the fastest athlete from a group of athletes through a given drill may be determinable, these known systems do not allow that athlete to be meaningfully compared to athletes from a category of individuals that may not have participated in the drill on the exact same day.

BRIEF SUMMARY OF THE INVENTION

In a first aspect, the invention provides the athlete and trainer a training and evaluation method that allows them to view their performance with respect to other athletes within their skill level and within a broader overall category of athletes that compete within a training group. The need for a customizable universal athleticism rating system and related athletic performance measuring systems for accurately detecting and recording athletic performance is needed to provide a common and quantifiable grading means. While no system can overcome the graders biases, a system is needed to help alleviate the effect of the bias and provide an accurate baseline for all athletes both within a skill level group and within a category. Among other benefits disclosed herein, the present invention fulfills these needs.

The instant invention is a system that automatically assigns a score from 1-100 using a range of results dictated by an Account Administrator and void of any limitations based on measuring unit type (time, distance, weight, repetitions etc.) or measuring unit (inches, pounds, kilometers etc.) using an algorithm. The result is that the instant invention makes the variation between sport and skill level a non-factor and as a result, it creates a platform that any club, organization or sport can use to track results based specifically on the way they perceive their needs are to enhance the performance of their athletes.

In a disclosed embodiment, an athleticism rating system evaluates individual athletes against a common set of athletic performance tests. In general, each athlete performs the athletic tests and his or her scores in the individual tests are entered into a standardized calculation to produce an athletic performance score. This score can then be compared to the athletic performance scores of others who also completed the tests, thereby providing an objective rating of athletic performance between competing athletes.

The system also provides a means of creating a competition amongst the athletes by providing a leader board mechanism which displays the results and scores for each individual test and their overall score for the group of tests.

In another disclosed embodiment, the performance measuring system integrates with the rating system to provide seamless athletic data collection and rating of athletes.

BRIEF DESCRIPTION OF THE DRAWINGS

A further understanding of the nature and advantages of embodiments may be realized by reference to the remaining portions of the specification and the drawings, in which like reference numerals are used to refer to similar components. When reference is made to a reference numeral without specification to an existing sub-label, it is intended to refer to all such multiple similar components.

The invention will now be further described by way of example only, with reference to the accompanying drawings, in which.

DETAILED DESCRIPTION OF INVENTION

Figure 1:
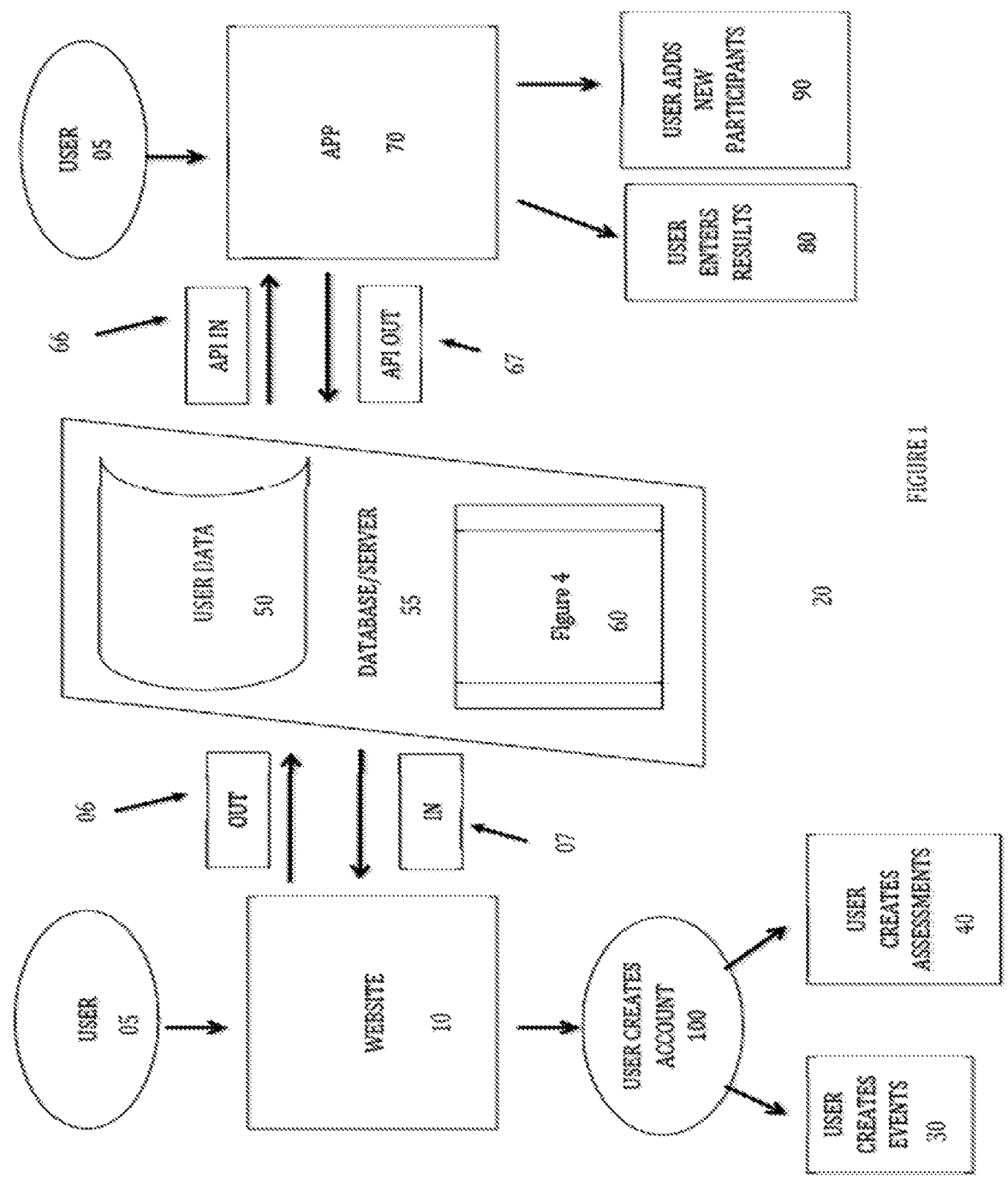
FIG. 1 is a flow diagram showing the overall system components of the invention.

While various aspects and features of certain embodiments have been summarized above, the following detailed description illustrates a few exemplary embodiments in further detail to enable one skilled in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

In this application the use of the singular includes the plural unless specifically stated otherwise, and use of the terms "and" and "or" is equivalent to "and/or," also referred to as "non-exclusive or" unless otherwise indicated.

Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Numerical values for dimensions, volumes and masses in this specification are shown in U.S. customary units.

The use of the term event administrator, administrator, coaches, personal trainers, athletic organizations, user, coach, athlete, and trainer when used is synonymous with and include a person.

The use of the term monitor when used is synonymous with viewing display.

The use of the term grade or score when used are synonymous with individual result of a test or an event.

The use of the term data collection, inputting data and uploading data when used is synonymous with data collection.

The use of the term displaying data, printing, downloading data when used is synonymous with displaying data.

The use of the term algorithm, system, application, APP, website, software system, and program when used is synonymous with the method of using standalone program on a non-specialized computing device or specialized tablet device to accomplish a specific or a group of specific tasks.

The use of the term computer, laptop, desktop, server, smart phone, personal digital assistant, tablet, computer, smart device or calculator when used is synonymous with specialized tablet device.

The invention is particularly useful because it provides a method of normalizing and evaluating different athletes with varying athletic skills so they can be viewed and compared to one another.

An athleticism rating system and related athletic performance measuring system 20 are described herein and disclosed in FIGS. 1-5. The athleticism rating system evaluates individual athletes against an athletes' definable skill tests which are common such as events such as running, weight lifting, jumping, swimming, walking, and cycling or other standardized tests or a custom set of athletic performance tests. The related performance measuring system 20 is preferably a user configurable software system that ensures quick, easy, and accurate collection of athletic event data. In one disclosed embodiment, the performance rating system 20 provides seamless athletic data collection and rating of athletes. Each of these aspects of the invention are discussed in greater detail below.

Athletes, coaches, personal trainers, and athletic organizations have been testing athletes to determine the skill and athletic capability of the various individuals. They all want to know how their athletes are performing, how they compare to other athletes and most importantly what areas they need to improve. For years, the most common method of recording the results was writing the results down on a clipboard as the athletes performed the athletic tests. This helped the coaches analyze the results and put together a plan for the athlete moving forward. However, using this method of recording results limits those that can view the results. The athletes, their parents, other coaches, athletic trainers, or recruiters do not have the ability to view or analyze the results. This can frequently cause confusion as the results of the athletic tests are not accessible to all parties associated with the athletic event.

Eventually, coaches evolved and started entering the results into spreadsheet applications and other systems to provide a more automated means of collecting and viewing the data, which helped them organize the results and potentially share the results with others via email or posting them to a website. The result of this method was much better than the traditional paper and pen clipboard model, but it was very labor intensive and time consuming. The coaches would still have to write the results down on a clipboard, then once all the athletes were done, someone would have to manually type all the results into a spreadsheet for dissemination to the various concerned parties. Once everything was entered into the spreadsheet application, they would have to individually email out all of the results, or post them to a website where people could go to view them.

The instant invention solves these problems with a simple and efficient way to set up an event, record results, and have those results be viewed in real time by anyone who is authorized to review them. The invention allows the user to create an event which is comprised of one or more tests and these tests can then be graded and displayed individually or as a composite score. The technology not only allows results to be entered and displayed through a mobile application on a specialized tablet device 3000 (comprising of tablet surface and processor system 3010 and holder 3020), smart device, smart phone or tablet in real time, but each result is associated with a score and ranks the athletes in order on a leaderboard, so a specific athlete's performance is available and they can see how that athlete performed with respect to the group or isolated to just the specific individual. Each individual athletic test has a leaderboard and once all the tests have been completed, a leaderboard with overall scores for the entire event are automatically generated.

The instant invention eliminates clipboards by giving the coaches the ability to enter all data electronically through the mobile application on their specialized tablet device 3000, smart device, smartphone or tablet thereby eliminating all manual entry processes and the resulting errors that such data entry systems are susceptible to.

The instant invention eliminates redundant data entry steps because the data needs to be entered only once on the mobile application which can be accessed from any location such as the gym, the track, weight lifting facility, etc.

The instant invention results in eliminating posting or emailing of results because all results are visible in real time on the mobile application to any user that has the necessary privileges to view the data. The results automatically populate the data via modules and are then displayed onto leaderboards as they are entered into the system.

The other feature of the instant invention is that it provides a unique and beneficial advantage to coaches and trainers and provides them the flexibility to create their own grading criteria and athletic tests for an event. There are systems that exist that have a certain set of predetermined athletic tests and scoring scales that coaches can use to test their athletes. However, these systems are very restrictive for coaches because every coach is different and every sport is different. The instant invention eliminates these drawbacks by providing the coach the flexibility to create the testing criteria that are unique to their sport, athletes, and coaching style and as such provides them with a competitive advantage. For example, a swim coach will want to test different things than a football coach. There are criteria that a swim coach will want that are extremely relevant to swimming, but completely irrelevant to football. For example, a 40-yard dash is a great test for speed in football, but will mean absolutely nothing to a swimmer. By giving a coach or athlete the ability to customize their events to suit their needs, it will promote the continuing improvement for a specific athlete or group of athletes.

The instant invention allows the coach to determine what athletic tests will be in the event when it is created and the flexibility of the system gives the coach the ability to add tests, modify tests or add participants after the initial creation of the event. The coach also determines the score for each test, which ultimately feeds into the overall score for the event. Coaches require a real-time data entry process and they need to be able to create new events quickly and have the flexibility to change and modify criteria. The instant invention can do this because the instant invention does not limit the coach to only a certain set of predetermined tests. The coach has the freedom to test what they want when they want and with whom they want.

The instant invention is a system that automatically assigns a score from 1-100 using a range of results dictated by an Account Administrator and allows the administrator to utilize any measuring unit type (time, distance, weight, repetitions etc.) or measuring unit (inches, pounds, kilometers etc.) they want using an algorithm built into the system. The result is that the instant invention has the effect of making the sport and skill level a non-factor and as a result, it creates a platform that any club, organization, or sport can use to track results based specifically on the way they perceive their needs and to enhance the performance of their athletes.

For example, if an organization tests their athletes every 6 weeks and this organization has 3 skill levels of athletes (Youth, Collegiate and Professional) in their membership, the organization can have all their athletes perform the same tests to measure their performance. The invention allows the administrator to measure the skill levels and rank them according to different criteria instead of measuring all skill levels based on the exact same criteria. The program Administrator decides to adjust the grading criteria for the youth so that the results that yield a score of 1-100 are better represented based on the results that their Youth Group has achieved in the past. As a result, even though all the athletes regardless of skill level take the same tests, the results that yield the scores associated will differ based on the specific needs of the program Administrator.

The key elements of the instant invention are:
1) Event Creation
2) Individual Test Creation
   i. Add an unlimited number of tests of your choice. Can create custom tests
   ii. Select measuring unit type
   iii. Select measuring unit
   iv. Assign a LOW score result (will=1 on grading scale) and a HIGH score result (will=100 on grading scale)
3) Grading scales are automatically generated when you press submit
4) Upon entering results for all the tests, cumulative score is generated based on average of all results The instant invention system is an online platform that gives the athletic event administrators an online tool to create athletic events that are made up of several individual athletic tests of their choice. Each individual athletic test within the event is assigned a high result (a result greater than or equal to a specific score and will be assigned a completion value of 100), which equals a score of 100 on the scoring scale. The assigned low result (a result less than or equal to that would register as one) equals a one on the scoring scale. Once the high and low results have been defined, entered and submitted, a full scoring scale is generated by the system and the invention assigns results with scores based on the high and low results entered ranging from 1-100. All results for the individual athletic tests will fall somewhere between 1-100. When an athlete completes the athletic tests, they receive both the result and the associated score that is automatically generated and displayed on the scoring scale between 1-100 for the tests. Once the athlete has completed all the athletic tests within the event, the instant invention generates an overall blended score for the event which is an average of the scores associated with each individual test. Alternatively, the invention can allow the program administrator flexibility to weigh a certain test more or less than another test in the same event to control how the overall score is calculated.

The web based online tool gives the event administrator full control of their account where they will be able to manage their events and control how people will view their events on the Mobile Application which provides other authorized parties the ability to view results of the event/test. The program administrator has the ability to upload a roster for the event, so everyone on the roster will appear on the event leaderboard on the mobile application. The program administrator can also assign specific ID's associated with the participants, and control if the event can be seen or hidden from public view. The mobile application can also allow the event administrator to add an athlete at the event even if they were not on the original roster.

Once the program administrator has created the athletic event, created the individual athletic tests with scoring scales for the tests, and uploaded a roster, they are ready to start entering results for the athletic event on the mobile application.

The athletic event that is created on the website can now be viewed in the event administrator's account on the mobile application. The event administrator can now sign-in to the event and start entering the results for the athletes on the roster for the event. Once a result is entered for an individual, that result will appear on the leaderboard for that individual athletic test. The leaderboard is comprised of every athlete on the event roster as well as those that were added at the event in alphabetical order by name, numerical order if athletes are displayed by their athlete ID, or by any other listing methodology that is applicable. As results are entered, the leaderboard will automatically display the results and associated scores from highest to lowest. The leaderboard will display a "DNF" (Did Not Finish) for all participants that have not registered a result for every individual test. When an athlete completes all of the individual athletic tests within the event, they will have a result and score on the leaderboard for each test as well as an overall score for the event. The administrator can assign a value for all DNF entries so that an overall score can be determined.

The event administrator determines whether they want the leaderboard to display the athlete's names or display the assigned athlete ID. Alternatively, the event administrator can define any identity identifier that is suitable for the event or participants. The main leaderboard on the mobile application will display the overall score, but there is also a leaderboard for each individual athletic test. The leaderboard allows an athlete to evaluate their performance for each test in the event with respect to the roster of athletes and the overall score provides an overall evaluation metric for the athlete with respect to the roster of athletes participating in the event. The software module that controls displaying specific test results can organize them with respect to the leaderboard for the entire event or within a specific test. This allows the observer to scan all the participants and see who is leading the event or the specific test. Additionally, this allows the athlete and the coach to evaluate specific test results within an event with respect to the roster of participants. The athlete can also use this functionality to compare themselves to the entire roster with respect to the individual test or the combination score of all the tests in the event. All the individual leaderboards also allow the athlete to check on any athlete on the leaderboard which allows them to view the athlete's results for the specific athletic event or individual test. The display module also allows the user to view results for individuals and is capable of showing all the results and scores for the event for a specific athlete or group of athletes.

The mobile Application gives the event administrator the option of sharing their event privileges with other registered users. An example of this is to extend privileges so another coach can assist in entering results for that event. The event administrator accomplishes this by sharing the administrative privileges with the individuals there by safe guarding their password but allowing others to help with the data entry for the event. The event administrator can then revoke the privileges when it is no longer appropriate.

The administrator or individual who has the proper privileges can use the mobile or website application to enter results for that selected athlete. After entering the test results for a specific athlete, they can submit the results and the associated scores will be visible to any registered user with the correct privileges on the leaderboard. The results will be displayed in order from high to low with all of the other results that were entered. However, the invention allows the event administrator to override the display order and substitute a format which meets their needs such as by age or by sex.

The website key elements include:
1) Athletic Event Creation.
2) Individual Athletic Test Creation.
3) Scoring Scale for Test Creation.
4) Upload roster for athletic event participants.
5) Name display, and Athlete ID display control.
6) Assign custom password for events.

The mobile application key elements include the following features:
1) Enter results for athletic test.
2) Share administrator password with other coaches to help enter results.
3) Add athletes to roster at the event.
4) View results on the leaderboard.
5) View Overall results as well as results by individual athletic test.
6) View all results for an individual by clicking on the name.

The following functions are provided by the software:
1) Account is created on website and personalized.
2) Athletic event is created on website.
3) Individual athletic tests are created within event.
4) Scoring scales from 1-100 are created for each test with HIGH/LOW results.
5) Roster is uploaded for the event.
6) Event Administrator determines name display or Athlete ID display on leaderboard.
7) Event is submitted and appears in the UAT+mobile App.
8) Administrator logs-in to the event on the UAT+mobile App.
9) Administrator grants other coaches permission to log-in.
10) Coaches click on Name of Athlete ID and enter result for the test and submit.
11) The result appears on the leaderboard under the specific test tab.
12) The results populate in order from Highest to Lowest for each test.
13) Once a result is entered for an athlete the leaderboard display changes from "DNF" to the result.
14) Once all results are entered an overall score is generated and displayed on the leaderboard.
15) If a name is clicked on, a box will pop up that that shows all the results for that athlete.
16) Once the event is completed, the event administrator can log-in to their account online and export all the results from the event to an XLS format for use with a spreadsheet and for storage on their computer.

What makes the instant invention unique when viewed with respect to the current prior art is that the instant invention empowers the administrator by placing total control for the testing, the assembling and displaying of results in the hands of the administrator. The online platform gives the event administrator the ability to customize their event, customize all the individual athletic tests within the event and customize the scoring scales for each athletic test and assessment. The invention allows for significant customization of events and tests within an event and it does not force the Administrator to use predetermined tests or assessments, but instead the invention empowers them by giving them a tool to create their own set of tests and assessments to enhance their own practices. The predetermined athletic tests are 40 Yard Dash, Vertical Jump, Bench Press, Shuttle Run, Broad Jump, and 1 Mile Run. However, the invention allows the event administrator to add or customize their own tests as needed which provides the event administration significant flexibility in creating tests that specifically meet their needs and the needs of their athletes.

The mobile application (App) which can reside on a smart phone, tablet, specialized tablet device 3000, smart device, personal digital assistant, or a similar mobile computing device also gives the event administrator the ability to have a single point data entry functionality. The mobile application also gives the event administrator the ability to display results as they are entered into the mobile application in real time. Furthermore, the mobile application gives anyone who has downloaded the App the ability to view results on an event leaderboard in real time as they are entered by the coaches. They can view the leaderboard for each specific athletic test in the event as well as the overall score leaderboard. They can also interrogate an individual athlete's results by accessing the data from the athlete's name or athlete ID which allows them to view all the results and scores for that athlete in the event.

The instant invention is further differentiated from the prior art because it puts the control for entering, organizing, grading/scoring, weighing, and displaying in the hands of the administrator. The online platform gives the event administrator the ability to customize their event, customize all the individual athletic tests within the event, and customize the scoring scales for each athletic tests and assessments. What sets the invention apart is that the invention does not attempt to create an assessment for the clients. Instead the invention empowers them by giving users a tool to enhance their own practices.

The mobile application of the invention further provides the event administrator the ability to have a single point of data entry functionality. The mobile application also gives the event administrator the ability to display results as they are entered into the mobile application (App) in real time using their specialized tablet device or smart phone device. The mobile application gives anyone who has downloaded the App and has the correct privileges the ability to view results on an event leaderboard in real time as they are entered by the coaches. They can view the leaderboard for each specific athletic test in the event as well as the overall score leaderboard. By accessing the data by athlete's name or athlete ID they can view all the results and scores for that athlete in the event.

Specifically using FIGS. 1-5 a system 20 is disclosed. The user 05 can alternatively access the system from either the website 10 from a computer, laptop, server, tablet, smart phone, specialized tablet device 3000, smart device, personal digital assistant, or a similar mobile computing device or by using a mobile application 70 on a tablet, smart phone, personal digital assistant, specialized tablet device 3000, smart device or a similar mobile computing device. Specifically looking at FIG. 1 the user accesses website 10 and creates a user account 100 and with that account 100 they can create user events 30 and assessments 40. Alternatively, they can access the database server module 55 which contains the user/athlete/client data 50 and software 60 modules. The website 10 passes data to the database server module 55 using communication channels in 07 and out 06. The application 70 also provides access to end user results 80 and allows the user to add new participants through accessing module 90. The application 70 passes data to the database server module 55 using API in 66 and API out 67.

Figure 2:
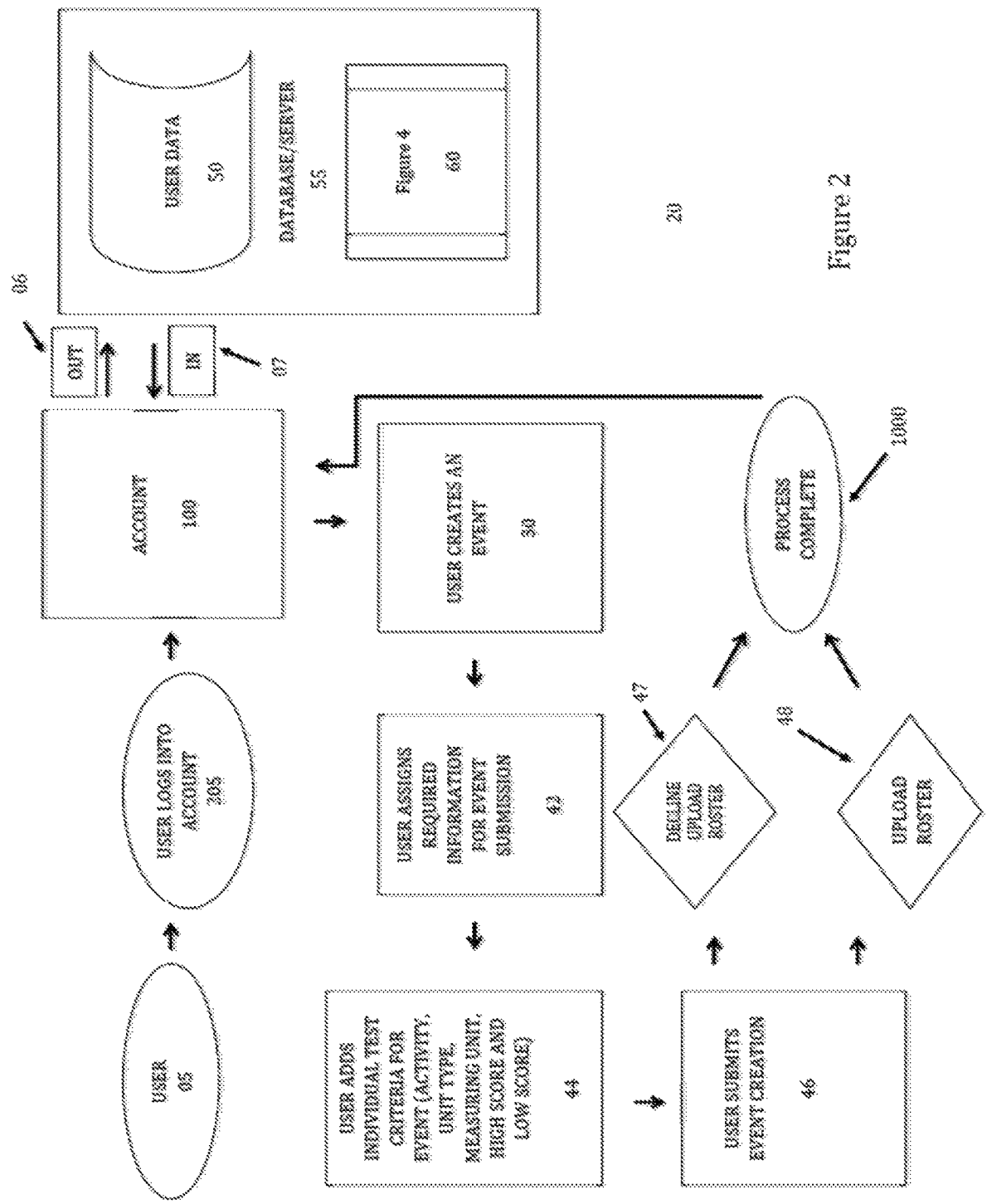
FIG. 2 is a flow diagram of the system used from a website.

As shown in FIG. 2 the user 05 logs into the user account 100 through user account login module 205. The user 05 then can create an event using module 30 wherein the user 05 assigns information and submits the event with module 42, adds individual test criteria for the event 30 such as activity, unit type, measuring unit, high score, and low score using module 44. Once the information has been entered into module 44 the user 05 submits the new event to the system using module 46 which also permits the user 05 to upload a roster of individuals that will participate in the event using module 48. If there is not a roster and this is an individual event then module 47 is selected and the event is uploaded without a roster associated with it. Once the roster and all athlete 50 information for the event is uploaded the process is complete and module 1000 transfers control back to the account 100 module.

Figure 3:
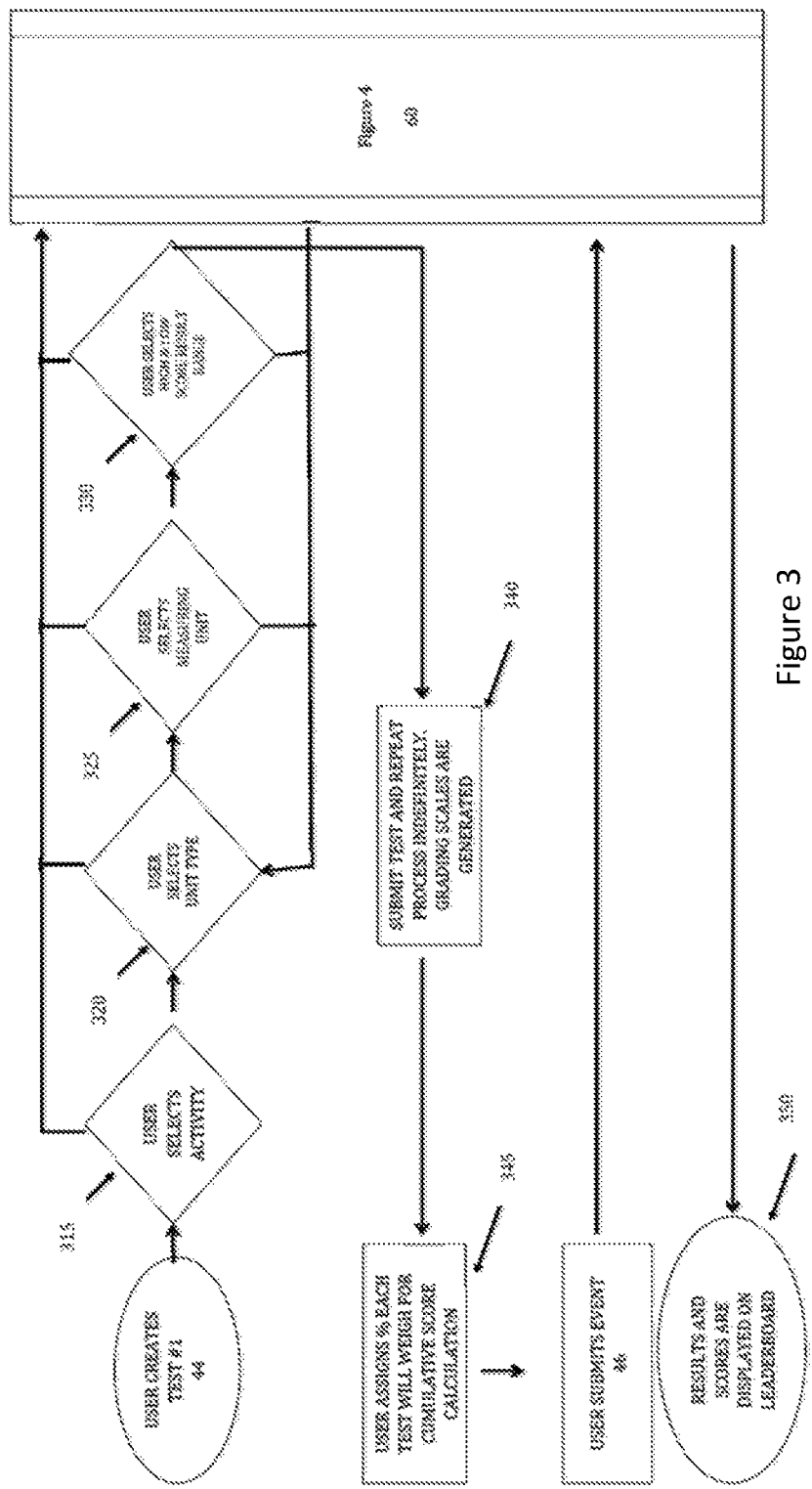
FIG. 3 is a high-level flow diagram showing the invention and rating system.
Figure 4:
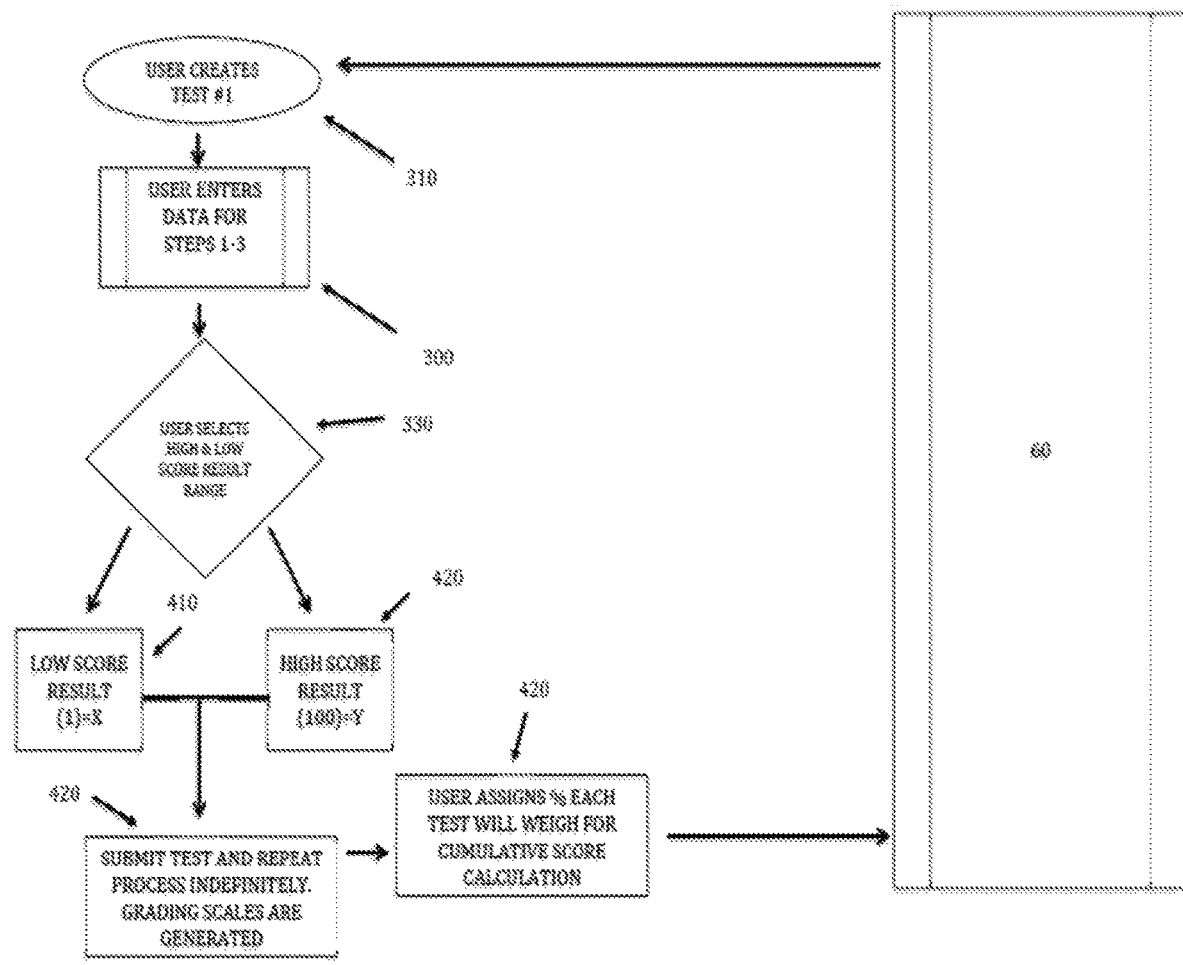
FIG. 4 is a flow diagram of the system showing the detail rating system.

Referring to FIGS. 3 and 4 the user 05 first selects a test from either of the six predetermined athletic tests provided by accessing module 315 to select a test activity. The predetermined athletic tests are 40 Yard Dash, Vertical Jump, Bench Press, Shuttle Run, Broad Jump, and 1 Mile Run. However, the invention allows the event administrator to add or customize their own test as needed which provides the event administrator significant flexibility in creating tests that specifically meet their needs and the needs of their athletes.

If one of the six predetermined athletic tests are not what is desired the user 05 can alternatively select Other from the dropdown menu and the user 05 can enter a unique name of the desired athletic test. The next step in the process is for the user 05 to select the test Unit Type using module 320 which is comprised of the activities measurement parameters of time, distance, repetitions, and weight. The user can then select the Measuring units using module 325 for the test/activity identified using module 315 which is comprised of multiple specific measuring unit options for the different test unit types. Once selected, the software associates specific measuring unit options with the selected unit type. These options are clearly displayed allowing the user 05 to choose a desired measuring unit such as pounds, kilograms, hours/minutes/seconds, feet/inches/meter etc. For example, weight could be measured in pounds or kilograms, time could be measured in hours/minutes/seconds or minutes/seconds or seconds etc. and distance could be measured in feet/inches or inches or meters, etc.

The user then needs to assign the low result and high result range for the test/activity created using module 315 using module 330. This results in the low score result being assigned a 1 by module 410 and the high score result being assigned a value of 100 by module 420.

After all the data is correctly inputted into modules 315, 320, 325, and 330, the unique data entered and/or selected is sent to the software module 60 where open data entry fields are assigned for the low result and high result based on the measuring unit selected. The software is enabled to accomplish this assignment in module 60 due to the hierarchy among measuring units that are comprised of multiple sub units and the software then places them in proper order to be displayed. If a measuring unit has more than one sub unit, the software module 60 identifies which is the highest unit of measure and arranges them to be displayed in order from highest unit of measure to lowest unit of measure. For example, if the activity/test is a 225-pound Bench Press test and repetitions is the Unit of Measure selected for this test, then the software module 60 will assign a one to the open data entry field. Another example that illustrates this function is if the activity/test is a 5k running race and the unit of measure selected is minutes/seconds, then the software module 60 will infer that there are two open data fields, one for minutes and one for seconds and that the minutes field is the highest unit of measure. Additionally, if the activity/test is a marathon running race and the unit of measure selected is hours/minutes/seconds which results in three open data entry fields, the module 60 will assign hours as the highest unit of measure and place all subsequent units of measure in the appropriate order.

Module 60 utilizes rules when assigning open data entry fields. After module 330 data entry has been completed and the module 60 has determined the hierarchy of the selected measuring units, the software module 60 will now apply data entry rules for each open data entry field. The software module 60 will assign a list of parameters based on the specific measuring unit selected in module 325. The parameters are designed to provide a set of rules for data entry for users. The parameters applied are as follows within the module 60. First, software module 60 will only allow a maximum of 6 characters to be entered into each of the open data entry fields. Characters may only include numerical values and one decimal. When more than one open data entry field is assigned to a measuring unit, the highest unit of measure entry field result can exceed the predetermined parameters for that specific measuring unit, but cannot exceed the overall numerical maximum of 6-digit integer represented by a maximum value of 999999. For example, there are 60 minutes in an hour, which would be the standard predetermined parameter for minutes. However, if the measuring unit minutes/seconds was selected for the measuring unit, minutes would be considered the highest unit of measure and would be exempt from the standard predetermined parameter of 60 minutes, and would only be held to the overall numerical maximum of 999999. Therefore, the result could post 153 minutes up to 999999 minutes. The same would apply if a standalone Measuring Unit is selected i.e. "minutes" without any additional sub units.

When more than one open data entry field is assigned to a measuring unit, module 60 recognizes that any data entry field other than the determined highest unit of measurement data entry field will follow the standard predetermined parameter assigned by the proprietary software for that specific measuring unit. Therefore, utilizing the previous example, if we selected the measuring unit minutes/seconds in software module 325, the module 60 will configure the test/activity such that seconds would not be considered the highest unit of measure and would be subject to the predetermined parameter of 59.59 seconds. Another example would be if minutes/seconds were the selected unit of measure for an activity/test, the result could be expressed as 75 minutes and 12 seconds whereas if the same event is assigned hours/minutes/seconds as the unit of measure the result would be displayed as 1 hour, 15 minutes and 12 seconds.

An example of the unit of measure reconciliation rule in module 60 is if minutes/seconds is selected as the measuring unit in module 325, then module 60 will assign the highest unit of measure value to minutes and therefore the minute unit of measure will be exempt from the predetermined maximum parameter of 59 Minutes. Since there are a total of 60 minutes in 1 hour but because minutes was selected as the highest unit of measure the minute field is not restricted to a maximum of 60 minutes.

If measuring unit is selected as hours/minutes/seconds in module 325, then module 60 will assign the highest unit of measure value to hours and the minute field would be held to a preassigned maximum of 59 minutes because it is no longer the largest unit of measure. Module 325 and module 60 are limited to floating point numbers with a maximum of two decimal places such as 59.59 for 59 minutes and 59 seconds.

The next function of module 60 is to assign the low and high result which were entered in module 330. The ability to create unique grading criteria allows the coaches/trainers to customize the events/test for their specific athlete/athletes. Module 60 allows the coach/trainer to track performance by creating their own customized method to track progress and performance with respect to an individual or a group, such as the roster created in module 48. The unique grading scale creation feature is important to the Administrators and athletes that utilize the instant invention, because it provides them with context in an easy to understand display via module 350. This feature provides transparency and performance evaluation because the data can be displayed using module 350 with the results and the scoring metric. For example, an athlete records a 32" vertical jump in an event, or using the invention they record the same 32" vertical jump which produces a score of 83 and ranks 11th out of 100 on their specific leaderboard roster group. The score of 83 and the rank of 11$^{th}$ provide context and understanding for the result of the 32" vertical jump. The instant invention module 60 allows for the processing and sorting of the information such that each individuals' performance can be displayed via module 350 with context so that the result has meaning.

In a real scenario, a facility with clients having a range of skills utilizes the same assessment for all their clients, but since the clients have different skill levels which range from young athletes, amateur, and professionals they want to weight the performance differently to reflect the skill level of the individual being tested. They would not want to base the scores for the young athletes at the same level as the professionals, because of the gap in skill level. Therefore, the instant invention allows the event administrator the ability to adjust the grading criteria based on their individual needs and overall skill level of the athletes.

The user will determine the low result for the individual tests using module 330. The LOW result will vary based on the level of athletes being tested. The invention normalizes the results by forcing any result less than or equal to the determined low result to be assigned a score of one.

The user will determine the high result for the individual tests using module 330. The high result will vary based on the level of athletes being tested. The invention normalizes the results by forcing any result greater than or equal to the determined high result to be assigned a score of one hundred.

Once the user has entered the low result and high result into module 330 they submit the data to module 60 by accessing module 340. Module 340 allows the user to add new activities and generate the associated grading scales. Because of the various data that can be supplied to the module 60 program there is an unlimited amount of scoring combinations because the range between high and low scores are flexible. The module 60 software will determine scoring increments for each individual test created, identify results for each of the grading increments, apply rounding rules and then allow the user to be tested and their results graded.

The module 60 Scoring Scale Creation: Once the data has been submitted to module 60, the software will subtract the low result value entered in module 330 from the high result value entered module 330 and then will divide the difference of those values by a value greater than or equal to 100. It is important to note that for the unit type "time", the high result will be subtracted from the low result to determine the scoring result differential. Module 60 is programmed to divide the difference in the results range into a value greater than or equal to 100 equal increments. Convenient values for this denominator are 100, 1000, and 10,000 which provide different levels of granularity to the final result. However, any suitable number can be used as the denominator. After the results are successfully divided by a value greater than or equal to 100 equal increments, the software will assign results to those values greater than or equal to 100 equal increments to the nearest hundredths decimal place (0.00). This scoring differential is what filters the scoring scale into equal scoring segments.

Module 60 utilizes the following formulas:
A=Low Result
B=High Result
C=Difference between High score result and Low score result
D=a value greater than or equal to 100
X=Score Differential (Is the incremental value greater than or equal to 100 equal increments within the created scoring scale from 1-100 to the nearest hundredth (0.00))

$$B-A=C$$

$$C/D=X$$

Module 60 utilizes a rounding rule and all results recorded are rounded to the nearest hundredth place value.

Reviewing actual test data and how it is displayed when utilizing the invention will illustrate the novelty of the invention. Let's utilize a test being defined as pushups with a measuring unit selected as repetitions and the low score designation of 1, and the high score designation or 100.

The athlete records a test result of 45.73 repetitions. If the algorithm utilizes a D equal to 100 this will result in a score for the test of 46.00 being recorded.

To show the sensitivity of the scoring algorithm if the same athlete records a test result of 45.73 repetitions. If the algorithm utilizes a D equal to 1,000 this will result in a score for the test of 45.70 being recorded.

Additionally, If the algorithm utilizes a D equal to 10,000 this will result in a score for the test of 45.73 being recorded.

The module 60 Scoring Scale Testing: After the input from modules 315, 320, 325, and 330 have been successfully submitted to module 60 and modules 410 and 420 of the specific test for the event have been submitted, the completed scoring scale will appear on the Test Creation segment of module 60 and will be displayed for viewing via module 350. The instant invention gives the user the ability to test the scoring scale by manually entering a result or moving the scoring dial to adjust the score. Once the scoring scale is satisfactory to the user and they have successfully submitted the test, that test is saved in the event.

The scoring dial gives the Administrator the ability to test the scoring values by manually moving the dial. As the Administrator moves the dial, the result in the result box will change and the score displayed via module 350 will change based on where the dial is positioned. This unique feature allows the Administrator to quickly and efficiently test the results and scores without having to manually enter any data.

Module 60 provides the user access to utilize a scoring dial or sliding scale to enter a result into the result box, the dial automatically moves to the corresponding position on the scoring scale. Also, the score associated via module 350 and the result entered appears in the score display section on the page. The Administrator can also manually enter data into the result box utilizing the alphanumeric input mechanisms of their device.

The add test function, which is part of module 310, allows the user to create a new athletic test after the previously created test has been submitted. This process can be repeated indefinitely until the entire event has been created. This allows the user to create an event that has running, jumping, weight lifting, etc. as the test references the same roster and leaderboard.

Once all the individual athletic tests have been added, the user will select the submit event module 46 and all the data for the event will be sent to the module 60. Module 60 will identify the number of individual tests within the event to register the variable "T". The module 60 will add up the scores for each individual test to find "X" which is the Cumulative Score. Once "X" has been determined, module 60 will calculate "Y" which is the Overall Score by dividing "X" by "T". Using module 345 the Administrator is capable of weighing tests differently thereby modifying the cumulative calculation for a score to represent the requirements of the event administrator. For example, if the event is a test of endurance then the result of a 1 mile race test would be weighted higher than the 40 yard dash test to reflect the greater endurance component of the 1 mile race.

The module 60 software can create a leaderboard for the event which will permit the user to review everyone on the uploaded roster via module 48 and display them via module 350. The module 60 software will also create an "overall score" index on the leaderboard display via module 350. The overall score is a blended score based on each individual test score. The module 345 allows the user to assign the percentage weight that each test will have in the overall score.

The best method to present the actual calculations is by way of example:
A=40 yard Dash Score, B=Broad Jump Score, C=1 Mile Run Score, D=Shuttle Run Score
X=Cumulative Score
T=Number of Tests in Event
Y=Overall Score $$A+B+C+D=X$$

$$X/T=Y$$

Therefore, if A=75, B=95, C=60, and D=45 then T=4 and X=sum of A+B+C+D=275 and Y which is the overall score would equal 275/4=68.75

Therefore, the leaderboard displayed by module 350 would display the individual results for each test: score of 75 for the 40-yard Dash result, score of 95 for the Broad Jump result, score of 60 for the Mile Run result, score of 45 for the Shuttle Run result, and an overall score of 68.75.

Figure 5:
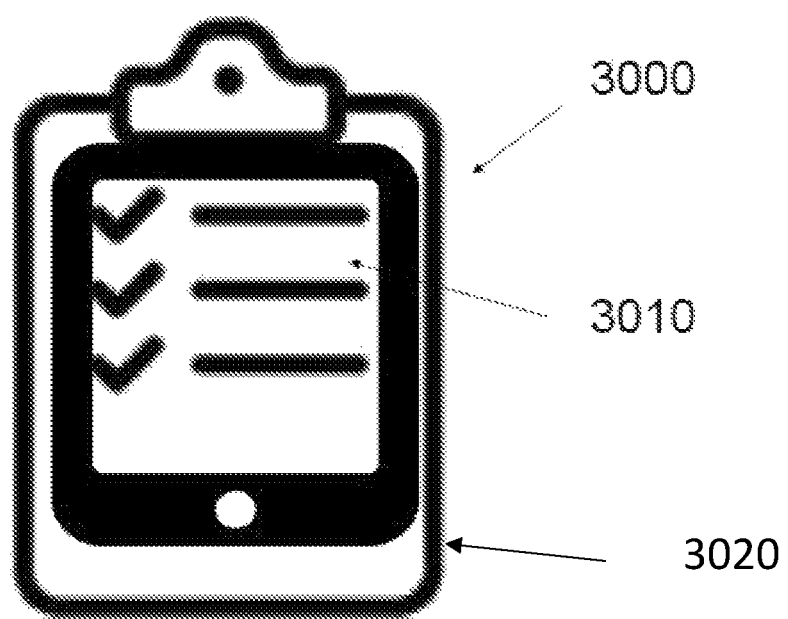
FIG. 5 is a view of specialized tablet device.

As seen in FIG. 5 the specialized tablet device 3000 comprising of tablet surface and processor system 3010 and holder 3020.

It will be appreciated that the illustrated invention has the great practical advantage in the management of athletic skills and management of athletic events for skilled athletic professionals and their athletes. In accordance with a preferred aspect of the invention, however, the data may be transmitted online, via the internet or other network means, to another location for review and analysis. Which provides the manager or administrator the ability to honestly rank athletes and provide the athletes on the roster with the ability to get an accurate view of their performance with respect to other athletes on a specific roster.

While certain features and aspects have been described with respect to exemplary embodiments, one skilled in the art will recognize that numerous modifications are possible. Further, while various methods and processes described herein may be described with respect to particular structural and/or functional components for ease of description, methods provided by various embodiments are not limited to any particular structural and/or functional architecture.

Hence, while various embodiments are described with or without certain features for ease of description and to illustrate exemplary aspects of those embodiments, the various components and/or features described herein with respect to a particular embodiment can be substituted, added, and/or subtracted from among other described embodiments, unless the context dictates otherwise. Consequently, although several exemplary embodiments are described above, it will be appreciated that the invention is intended to cover all modifications and equivalents within the scope of the following claims.

We claim:

1. A method for quantifying the athletic ability of an individual or group of individuals by evaluating performance of an individual with regards to an athletic test using a grading scale and inputting the data into a computer program on a specialized tablet device comprising of the following:
    a. Defining at least one event,
    b. Select a leaderboard event designation,
    c. Selecting at least one type of athletic test,
    d. Assigning a test value equal to the number of tests selected in step c and store said test value in register A,
    e. Assigning an identifier name for each said athletic test of step c and store the identifier names in array test units row one having register A columns such that only one identifier name is in each row one column which equates to one position for each test,
    f. Assigning a unit type to each athletic test of step c and store the unit type in array test units row two and having register A columns such that only one-unit type is in each row two column which equates to one position for each test,
    g. Assigning measuring units to each athletic test of step c and store in row 3 of test units array such that measuring units in row 3 and having register A columns such that only one measuring units is in each row 3 column which equates to one position for each test,
    h. Creating a roster of said individuals wherein the roster contains at least one roster individual identifier,
    i. Assigning a roster value equal to the number of said individuals in said roster of step h and stored said roster value in register B, assign the leader board array having register A plus one columns and register B rows,
    j. Assigning low grade criteria for each said athletic test of step c, wherein the low-grade value is selected from the values between one and one hundred,
    k. Storing low grade value in row four of test units array such that low-grade value in row four column one is associated with identifier name in row one column one, said low grade value being assigned a one on said grading scale,
    l. Assigning high grade criteria for each said athletic test of step c, wherein the high-grade value is selected from the values between one and one hundred,
    m. Storing high grade value in row five of test units array such that high-grade value in row five column one is associated with identifier name in row one column one, said high grade value being assigned a one hundred on said grading scale,
    n. Calculating said grading scale equal to the test range difference between said low grade and said high grade for each athletic of step c and store said grading scale value in row six of test units array such that said grading scale is stored in row six column one is associated with identifier name in row one column one,
    o. Set roster index one register to one,
    p. Set test index two register to one and register E to zero,
    q. Testing said individual from roster of step h using said type of said athletic test of step c and assigning a test grade based on said test range difference in test units array of step n and said low grade value of step k and said high grade value of step m,
    r. Adding said test grade form step q for said individual in register E,
    s. Adding the test grade from step q to leader board array column (one +test index two) and row (test index two) of leader board array,
    t. Add one to test index two register and compare it to Register B value, if test index two register is less than Register B then repeat steps o through r for the next individual identifier on said roster of step f,
    u. Dividing Register E of step r by (test index-) to create an overall score and storing it in row (one) column (one +test index two),
    v. Add one to index one register and compare it to Register A value, if index one register less than Register A then repeat steps o through v for the next individual identifier on said roster of step f,
    w. Displaying said leaderboard array and array test grades.

2. An athletic test of claim 1 wherein, the athletic test is selected from a predetermined list of events selected from the group consisting of running, weightlifting, jumping, swimming, walking and cycling.

3. A measuring unit for said athletic test of claim 1 wherein, the measuring unit for said athletic test is selected from the group consisting of minutes, hours, seconds, pounds, kilograms, repetitions, miles, yards, meters, feet, and laps.

4. A measuring unit of claim 1 wherein, the measuring unit is assigned the LOW Result identifier to the smallest measuring unit selected.

5. A measuring unit of claim 1 wherein, the measuring unit is assigned the High Result identifier to the largest measuring unit selected.

6. A grade of claim 1 wherein, the grading scale is further divided into ten thousand equal increments.

7. A leaderboard test grade of claim 1 wherein, the grading differential is calculated by taking the low grade and subtracting it from the high grade and dividing the difference by ten thousand.

8. The method of claim 1 wherein the user inputs the information into the computer program from a website.

* * * * *